United States Patent [19]

Wilson

[11] Patent Number: 5,589,451
[45] Date of Patent: Dec. 31, 1996

[54] METHODS AND TREAMENTS FOR CORNEAL HEALING WITH HEPATOCYTE AND KERATINOCYTE GROWTH FACTORS

[75] Inventor: Steven E. Wilson, Plano, Tex.

[73] Assignee: Board of Regents, The University of Texas System, Austin, Tex.

[21] Appl. No.: 947,683

[22] Filed: Sep. 21, 1992

[51] Int. Cl.$^6$ ............... A61K 38/18; C12N 5/06; C07K 14/485; C07K 14/475
[52] U.S. Cl. ............... 512/2; 530/399; 530/350; 435/240.2
[58] Field of Search ............... 424/85.1; 512/2; 435/240.2; 530/399, 350

[56] References Cited

U.S. PATENT DOCUMENTS 5,032,575  7/1991  Neufeld ................... 514/12

FOREIGN PATENT DOCUMENTS

PCT/US90/
  00418  1/1990  WIPO .

OTHER PUBLICATIONS

Stoker et al. Nature 327 pp. 239–242 May 1987.
Jacob et al. Eye vol. 3 sts pp. 618–625 1989.
Marchesi et al. J. Cell. Phys 144 pp. 326–332 Aug. 1990.
Wilson et al. Invest Opthalmol. U.S. Sci (US) 34(8) pp. 2544–2561 Jul. 1993.

Wilson et al., "EGF, EGF Receptor, Basic FGF, TGF Beta–1, and IL–1 Alpha mRNA in Human Corneal Epithelial Cells and Stromal Fibroblasts," *Investigative Ophthalmology & Visual Science,* 33(5):1756–1765, 1992.

Wilson and Lloyd, "Epidermal Growth Factor and Its Receptor, Basic Fibroblast Growth Factor, Transforming Growth Factor Beta–1, and Interleukin–1 Alpha Messenger RNA Production in Human Corneal Endothelial Cells," *Investigative Ophthalmology & Visual Science,* 32(10):2747–2756, 1991.

Dialog Search Report dated Jul. 20, 1992.

*Primary Examiner*—Mindy Fleisher
*Assistant Examiner*—David Schmickel
*Attorney, Agent, or Firm*—Arnold, White & Durkee

[57] ABSTRACT

The invention relates to the use of hepatocyte and keratinocyte growth factors for controlling the proliferation and motility of corneal cells in vivo and in vitro. It also relates to the use of these factors for maintaining the viability of the corneal cells during or after ocular surgery and during corneal preservation in storage medium prior to transplant. Polymerase chain reaction amplification has demonstrated that corneal epithelial and endothelial cells in vitro and ex vivo corneal epithelium produce messenger RNA coding for hepatocyte growth factor, hepatocyte growth factor receptor, keratinocyte growth factor, and keratinocyte growth factor receptor. Additionally, it was demonstrated that hepatocyte growth factor and keratinocyte growth factor stimulate the proliferation of corneal epithelial cells and corneal endothelial cells in vitro in a dose response manner.

13 Claims, 12 Drawing Sheets

METHODS AND TREATMENTS FOR CORNEAL HEALING WITH HEPATOCYTE AND KERATINOCYTE GROWTH FACTORS

The United States Government may have certain rights in the invention pursuant to the terms of grant EY 09389 awarded by the National Institutes of Health.

BACKGROUND OF THE INVENTION

1. Field of the Invention

The invention relates to methods of treatment for preservation and healing of corneal tissue. Compositions for such treatment comprise pharmaceutically acceptable compositions of hepatocyte and keratinocyte growth factors singly and in combination.

2. Description of Related Art

Corneal wound healing and the many factors which may promote or prevent it have been of concern to both clinicians and researchers. Opthomologists are frequently confronted with corneal dystrophies and problematic injuries that result in persistent and recurrent epithelial erosion, often with permanent endothelial loss. Many attempts have been made to use growth factors to stimulate healing of the corneal epithelium and endothelium following injury or surgery. However, only a limited number of approaches are currently available for treating patients who fail to heal epithelial injuries adequately.

Epidermal growth factor (EGF) is one substance that has been investigated as a means to stimulate the healing of corneal epithelium and endothelium following injury or surgery. This factor have also been tested as storage media for corneal preservation in attempts to improve the viability of corneal endothelial cells following corneal storage. The majority of the available in vitro and in vivo studies on corneal tissue have been performed with epidermal growth factor (EGF).

Many attempts have been made to use EGF to stimulate the healing of the corneal epithelium and endothelium following injury or surgery. Similarly, EGF has been added to storage media used for corneal preservation in attempts to improve the viability of corneal epithelial and endothelial cells following corneal storage.

Epidermal growth factor has been shown to stimulate the proliferation of bovine corneal epithelial cells in vitro (Gospodarowicz, et al., 1977). Similarly, in vivo animal studies have shown that epidermal growth factor stimulates corneal epithelial wound healing in the rabbit (Soong, et al., 1989) and rat (Brazzell, et al., 1991); Kitazawa, et al., 1990); Chung and Fagerholm, 1989; Reim, et al., 1988) after superficial epithelial wounding, keratectomy wounds of the anterior corneal surface, and corneal alkali burns. In two of these studies, however, there was increased vascularization (Chung and Fagerholm, 1989) and increased inflammatory response (Reim, et al., 1988) in the epidermal growth factor treated corneas compared with the control corneas. One randomized prospective trial of epidermal growth factor for the treatment of epithelial wounds (Kandarakis, et al., (1984)) demonstrated no difference between epidermal growth factor and vehicle alone in the rate of corneal epithelial wound healing after penetrating keratoplasty. Thus, despite the fact that epidermal growth factor has been available for over a decade, in vivo randomized trials have not demonstrated that epidermal growth factor stimulates corneal epithelial wound healing compared with controls.

The background for the use of EGF for the corneal endothelium is very similar. EGF stimulates in vitro proliferation or migration of bovine endothelium (Gospodarowicz, et al., 1977; Junquero, et al., 1990 and rabbit Raymond, et al., 1986; Joyce, et al., 1989). Similarly, epidermal growth factor stimulates the in vitro proliferation of human corneal endothelial cells (Nayak, et al., 1984). The use of epidermal growth factor in corneal preservation and intraocular use during eye surgery have been proposed (Neufeld, A. H., 1991). In two independent studies, however, epidermal growth factor did not stimulate the healing of cat corneal endothelium in vivo when epidermal growth factor was injected into the eye after cold-induced injury (Rich, et al., 1991; Brogdon, et al., 1989). A disappointing result was recently shown in a masked, randomized, prospective, multicenter trial in which paired corneas from the same donor were preserved in identical corneal preservation media with or without epidermal growth factor. There was no difference in the corneal endothelial cell counts between the epidermal growth factor and control groups at one or two years of follow-up (Lass, unpublished data).

The functional status of the endothelium and sustained corneal deturgescence after corneal preservation are also clinically important and are primary goals in the development of corneal storage media. Desirable storage characteristics include the extension of corneal preservation time, enhancement of corneal wound healing, and the reduction of normal progressive loss of endothelial cells post keratoplasty. In preserving corneas for transplants, for example, it is important that the endothelial cells remain viable and metabolically active and able to change to a mitotically active state after implantation.

The negative results obtained with EGF-stimulated corneal epithelial wound healing and corneal endothelial preservation in randomized prospective trials highlight a lack of other more effective agents to stimulate corneal epithelial and endothelial proliferation and preservation after wounding or during corneal preservation.

There is therefore a need to develop compositions that have a beneficial effect on corneal wound healing. While some studies indicate that EGF may have a beneficial effect in promoting epithelial cell proliferation, its effect on endothelial cell viability is problematic. Healing and preservation of both epithelial and endothelial cells is important, particularly the latter, because endothelial cell viability and function is fundamentally important in maintaining corneal clarity and vision during the aging process as well as after disease, surgery, or laser treatments. At present, only a limited number of approaches are available for treating patients who fail to heal either epithelial or deep wound injuries involving endothelial cell structure.

SUMMARY OF THE INVENTION

The present invention relates to compositions and methods employing hepatocyte and keratinocyte growth factors in maintaining corneal cell viability and promoting corneal cell proliferation. The methods are appropriate for treatment of corneal injury subsequent to accidental injury, surgical procedures affecting the cornea, and disorders of the cornea in which there are abnormalities of the normal healing process of the epithelium and endothelium. The disclosed hepatocyte and keratinocyte compositions are suitable for improving the viability of the corneal epithelium and endothelium during corneal preservation prior to transplantation of the cornea.

It has been discovered that keratinocyte and heptatocyte growth factors are surprisingly effective in promoting corneal cell proliferation. The inventor was aware that HGF was stimulatory for repair of liver tissue and for enhancing proliferation of some types of cells such as human keratinocytes. However, it was only after the discovery that hepatocyte growth factor, hepatocyte growth factor receptor, keratinocyte growth factor, and keratinocyte growth factor receptor were produced in human corneal epithelial cells and corneal endothelial cells that a role for these growth factors in regulating normal functions in human corneal epithelial cells and corneal endothelial cells was suggested. Once HGF and KGK in RNA were detected in corneal tissue, the inventor went further to demonstrate that exogenous hepatocyte growth factor and keratinocyte growth factor stimulated the proliferation of human corneal epithelial cells and human corneal endothelial cells. Surprisingly, both EGF and KGF stimulated corneal cells more efficiently than EGF. Even more unexpected was a dose response corneal cell stimulation within a range up to about 50 ng/ml, with subsequent inhibition at higher concentrations.

The present invention relates generally to methods of treatment employing hepatocyte and keratinocyte growth factor in promoting or regulating the healing or viability of corneal tissue following injury to the cornea or for any disorder of the ocular surface. The method generally involves treatment of corneal cells with an effective amount of hepatocyte growth factor in a pharmaceutically acceptable composition. This method is appropriate for treating both superficial and deep wounds; for example, wounds that affect either epithelial or endothelial cells. Such injuries include injuries to epithelial cells, corneal stromal fibroblast cells populating corneal center regions, and corneal cells located on the corneal posterior surface.

Specific disorders typically associated with epithelial cell damage and for which the disclosed compositions provide beneficial treatment include persistent corneal epithelial defects, recurrent erosions, neurotrophic corneal ulcers, keratoconjunctivitis sicca, microbial corneal ulcers, viral cornea ulcers, and the like. Surgical procedures typically causing injury to the epithelial cell layers include laser procedures performed on the ocular surface, any refractive surgical procedures such as radial keratotomy and astigmatic keratotomy, conjunctival flaps, conjunctival transplants, epikeratoplasty, and corneal scraping.

Pharmaceutically acceptable compositions of HGF or KGF may be applied topically to the ocular surface, either alone or in combination with other drug delivery systems; for example, in a hyaluronic acid solution or suspensions of collagen fragments. Particular formulations may be in the form of liquids, suspensions, ointments, complexes to a bandage collagen shield, or the like.

Pharmaceutically acceptable compositions of either KGF or HGF may be modified by the addition of the other growth factor. Thus, in a particular embodiment of a method for promoting corneal cell proliferation, both hepatocyte growth factor and keratinocyte growth factor may be included in pharmaceutically accepted compositions. Preferred compositions for corneal endothelial cell proliferation will generally employ relatively narrow concentration ranges of the growth factors. The range for optimal activities is between less than one nanogram up to about 50 nanograms per milliliter, as indicated from in vitro experiments on endothelial and epithelial corneal cells. A preferred concentration is about five to about ten nanograms per milliliter for either hepatocyte or keratinocyte growth factor-promoted stimulation of corneal cells.

Hepatocyte and keratinocyte growth factors are also useful in promoting healing of the corneal endothelium. This is particularly valuable for deep wound injury to the cornea in which the endothelium is significantly disrupted, such as following surgical procedures performed on the anterior segment of the eye or for disorders of the cornea in which there are abnormalities of the corneal endothelium. Examples of such disorders include Fuchs endothelial dystrophy, aphakic bullous keratopathy, pseudophakic bullous keratopathy, endothelial graph rejection, viral endotheleitis, iritis, and so forth.

KGF and HGF will also be useful in maintaining the viability or increasing the cell density of corneal endothelium following any surgical procedure performed on the anterior segment of the eye, such as cataract surgery, penetrating keratoplasty, intraocular lens insertion, intraocular lens exchange, iridoplasty, pupiloplasty, trabeculectomy, and so forth. In like manner, compositions containing EGF or KGF may be useful for preserving corneal tissue just prior to ocular surgery.

Also included in the invention are compositions useful for the preservation of corneal tissue. These compositions will contain an appropriate amount of hepatocyte or hepatocyte-like growth factor, optionally including keratinocyte or keratinocyte-like growth factor, in a tissue-compatible physiologically acceptable composition. A preferred amount of keratinocyte growth factor or hepatocyte growth factor to be used in these compositions will generally be between about one and about fifty nanograms per milliliter of each factor. However, amounts up to about 50 ng/ml may be useful in some applications where extensive proliferation is desired. Concentrations higher than about 50 ng/ml are typically found to be inhibiting; otherwise, up to about 50 ng/ml there is a dose response proliferation. One may desire to initiate proliferation with the appropriate dose, then inhibit proliferation by adding KGF or HGF until an inhibitory concentration is reached. Reinitiation of proliferation could be performed, for example, by dilution.

Compositions comprising keratinocyte and/or hepatocyte growth factor for several applications of in vivo treatment of human corneal disorders are also contemplated as part of the present invention. Where large amounts of epithelial tissue are destroyed the compositions are preferably administered topically. Administration may be in the form of a liquid, suspension, ointment, combination with a visco elastic agent or the like. Where extensive epithelial damage occurs, for example, the compositions may be administered intradermally or possibly subcutaneously, and this may be viewed as an internal topical administration.

The invention therefore is directed to compositions which include one or both of hepatocyte or keratinocyte growth factors and further to pharmaceutical compositions which include a pharmaceutically acceptable carrier. Suitable pharmaceutical carriers include, sterile aqueous solution, various organic solvents, emulsifying or suspending agents, or aqueous diluents such as water, ethanol, propylene glycol, glycerin or combinations thereof. Ophthalmic solutions for topical administration would be administered to the eye of the subject in need of treatment in the form of an ophthalmic preparation prepared in accordance with conventional pharmaceutical practice, see, for example, "Remingtons Pharmaceutical Sciences" 15th Ed., pg. 1488–1501 (Mac Publishing Co., Easton Pa.).

Ophthalmic preparations will contain one or both of the growth factors HGF or KGF, or pharmaceutically acceptable salts thereof in a usually preferred concentration of about one to fifty nanograms per milliliter. In many cases, about five to ten nanograms per milliliter will be preferred. Stimulation by as little as 1 ng/ml may also be appropriate where less extensive proliferation is desired. In a pharmaceutically acceptable solution, suspension, or ointment some variation in concentration will necessarily occur depending on the particular combination of growth factors employed, the condition of the subject to be treated and so forth. The person responsible for treatment will determine the most suitable concentration for the individual subject. Ophthalmic preparations will preferably be in the form of a sterile aqueous solution containing, if desired, additional ingredients, for example, preservative, buffers, tenacity agents, antioxidants, stabilizers, non ionic wetting or clarifying agents, viscosity increasing agents and the like. Additionally, other beneficial compounds may be added, such as cytokines, hormones or growth promoting agents.

Suitable preservatives for use in such a solution include benzalkonium chloride, benzethonium chloride, chlorobutanol, thimerosal, and the like. Suitable buffers include boric acid, sodium and potassium bicarbonate, sodium and potassium borates, sodium and potassium carbonate, sodium acetate, sodium biphosphate and the like, in amounts sufficient to maintain the pH between about pH 6 and pH 8, preferably between about pH 7 and pH 7.5. Suitable tonicity agents are dextran 40, dextran 70, dextrose, glycerine, potassium chloride, propylene glycol, sodium chloride, and the like such that the sodium chloride equivalent of the ophthalmic solution is in the range of 9.9 plus or minus 0.2%. Suitable antioxidant and stabilizers include sodium bisulfite, sodium metabisulfite, sodium thiosulfate, thiourea and the like. Suitable wetting and clarifying agents include polysorbate 80, polysorbate 20, poloxamer 282, and tyloxapol. Suitable viscosity increasing agents include dextran 40, dextran, 40, gelatin, glycerin, hydroxyethyl cellulose, hydroymethylpropyl cellulose, lanolin, methylcellulose, petrolatum, polyethylene glycol, polyvinyl alcohol, polyvinyl polyvinylpyrrolidone, carboxymethyl cellulose and the like. The ophthalmic preparation will be administered topically to the eye of the subject in need of treatment by conventional methods. For example, in the form of drops or by bathing the eye in the ophthalmic solution.

While the invention has been illustrated with keratinocyte and/or hepatocyte growth factor, it will be recognized that one need not employ only the growth factors, but that any active segment or compound with KGF or HGF-like properties may be substituted. One might identify and select suitable compounds by their binding affinities toward corneal cell receptors.

The source of KGF or HGF may be from natural sources, by synthesis or by production in recombinant cells. Some of these KGF or HGF-like compounds are likely to be more effective than intact KGF or HGF and in such cases one may expect optimal amounts for corneal cell proliferation to differ somewhat from the preferred range herein demonstrated for the intact factors.

In yet another aspect of the invention, compositions containing one or both NGF or KGF may be used to modulate corneal cell proliferation. It has been found that above about 50 ng/ml, EGF or KGF inhibits corneal cell proliferation. Thus, it is contemplated that one might attenuate corneal cell proliferation as desired attenuated by altering the concentration of EGF or KGF.

BRIEF DESCRIPTION OF THE DRAWINGS

FIG. 1A shows primary proliferative endothelial cells, primary senescent endothelial cells, SV40 large T antigen-transfected endothelial cells, ex vivo endothelium. Figure B shows primary epithelial cells, ex vivo corneal epithelium, embryonic lung fibroblasts (ELF), primary stromal fibroblasts (1), and first passage stromal fibroblasts (2). Mocks were amplified with samples that had undergone RNA preparation and cDNA synthesis without added tissue. Lane C is a simultaneous control amplification with water. Lanes marked with M indicate the φX174 Hae III markers. Lengths of selected markers in base pairs are provided to the left. The arrowhead indicates the product of the expected length of 378 base pairs. Hot blots of the same samples demonstrate the specificity of the 378 base pair PCR product.

FIG. 2A shows primary proliferative endothelial cells, primary senescent endothelial cells, SV40 large T antigen-transfected endothelial cells, ex vivo endothelium. FIG. 2B shows primary epithelial cells, ex vivo corneal epithelium, embryonic lung fibroblasts (ELF), primary stromal fibroblasts (1), and first passage stromal fibroblasts (2). Mocks were amplified with samples that had undergone RNA preparation and cDNA synthesis without added tissue. Lane C is a simultaneous control amplification with water. Lanes marked with M indicate the 100 base pair size markers. Lengths of selected markers in base pairs are provided to the left.

FIG. 3A shows primary proliferative endothelial cells, primary senescent endothelial cells, SV40 large T antigen-transfected endothelial cells, ex vivo endothelium (ex), embryonic lung fibroblasts (ELF), primary stromal fibroblasts (1), first passage stromal fibroblasts (2). FIG. 3B shows primary epithelial cells, and ex vivo corneal epithelium. Mocks were amplified with samples that had undergone RNA preparation and cDNA synthesis without added tissue. Lane C is a simultaneous control amplification with water. Lanes marked with M indicate the 100 base pair size markers. Lengths of selected markers in base pairs are provided to the left.

FIG. 4A shows primary proliferative endothelial cells, primary senescent endothelial cells, SV40 large T antigen-transfected endothelial cells, ex vivo endothelium (ex), embryonic lung fibroblasts (ELF), primary stromal fibroblasts (1), first passage stromal fibroblasts (2). FIG. 4B shows primary epithelial cells and ex vivo corneal epithelium. Mocks were amplified with samples that had undergone RNA preparation and cDNA synthesis without added tissue. Lane C is a simultaneous control amplification with water. Lanes marked with φX and M indicate φX174 Hae III and 100 base pair size markers, respectively. Lengths of selected markers in base pairs are provided to the left.

DETAILED DESCRIPTION OF PREFERRED EMBODIMENTS

Figure 1A:
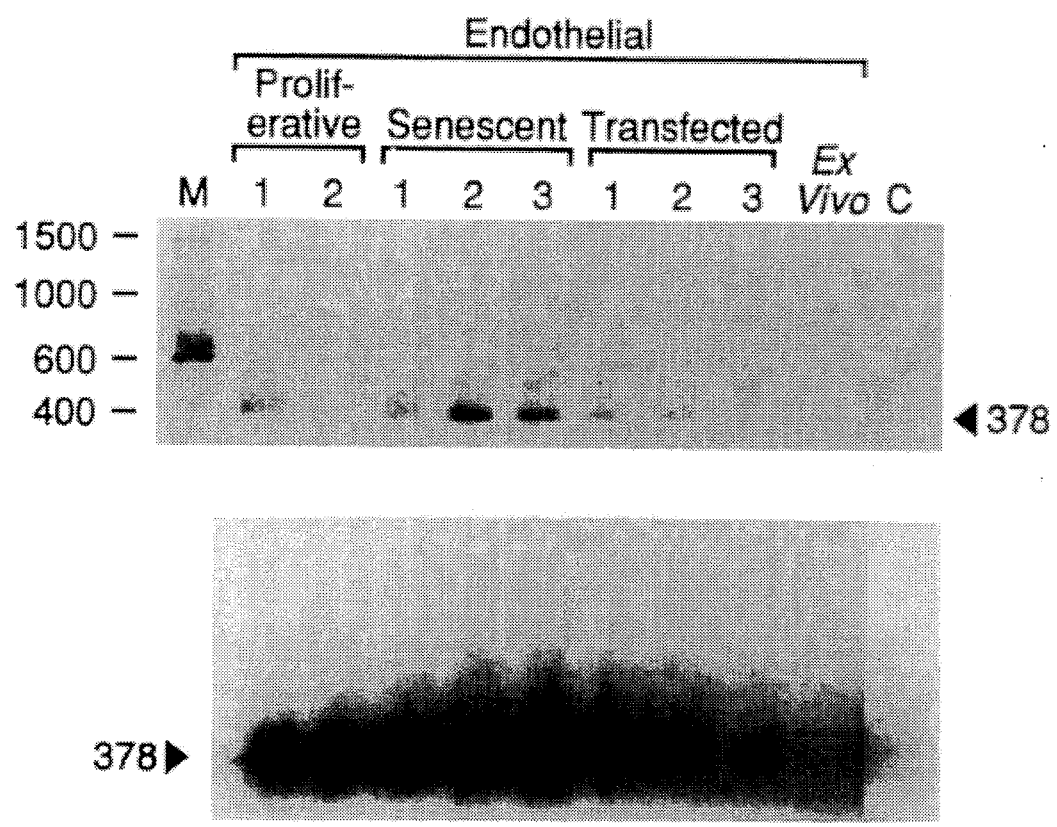
FIGS. 1A and 1B shows an ethidium bromide-stained agarose gel of hepatocyte growth factor PCR-amplified products that were amplified using the hot start method from the cDNA samples generated from human cells.

Two growth factors, keratinocyte growth factor and hepatocyte growth factor, have been previously characterized. These growth factors are naturally occurring substances that appear to have a role in controlling such functions as development, growth, motility, and viability of cells that produce the specific receptors for the growth factors. Keratinocyte growth factor is a member of the fibroblast growth factor family that was originally isolated from human embryonic lung fibroblast-conditioned medium (Rubin, et al., 1989). Keratinocyte growth factor stimulates the proliferation of keratinocytes [skin epithelial cells] (Marchese, et al., 1990), but has no effect on several lines of fibroblasts (Rubin, et al., 1989). High affinity keratinocyte growth factor receptors have been identified on Balb/MK keratinocytes, but not on NIH/3T3 fibroblasts (Bottaro, et al., 1990).

Hepatocyte growth factor is active in the repair of liver tissue (Monteasano, et al., 1991). It is identical to the scatter factor which stimulates the dissociation and scattering of epithelial cells (Gherardi and Stoker, 1990). Hepatocyte growth factor stimulates cell proliferation in such cell types as melanocytes and vascular endothelial cells (Rubin, et al., 1991). Hepatocyte growth factor has been shown to stimulate proliferation and migration of human keratinocytes (Matsumoto, et al., 1991). Hepatocyte growth factor receptor has been identified as the c-Met proto-oncogene product and has been detected in certain types of epithelial cells (Bottaro, et al., 1991; Prat, et al., 1991).

The present invention relates to methods and therapeutic compositions useful in corneal wound healing and preservation of corneal tissue. The compositions include hepatocyte and keratinocyte growth factor, neither of which has previously been associated with corneal tissue. The inventor has discovered that KGF and HGF may be used to induce corneal cell proliferation. This discovery resulted from experiments showing that KGF and HGF mRNA were present in corneal cells. Work by others had demonstrated the presence of HGF mRNA in vascular endothelial cells and liver Kupffer cells, but neither HGF nor KGF had been demonstrated in corneal cells. Once the presence of HGF and HGF in corneal cells was detected, the inventor determined that either or both of these factors stimulated corneal cell proliferation in a dose response manner. Moreover, such stimulation was effective at lower concentrations than EGF.

Generally, damage to corneal tissue, whether by disease, surgery or injury, may affect epithelial and/or endothelial cells, depending on the nature of the wound. Corneal epithelial cells are the non-keratinized epithelial cells lining the external surface of the cornea and provide a protective barrier against the external environment. Superficial wounds such as scrapes, surface erosion, inflammation, etc. mainly affect this type of cell. Endothelial cells, on the other hand, are found lining the internal surface of the cornea and most often are damaged by specific internal disorders, wounds to the posterior region of the cornea. Corneal endothelial cells maintain the clarity of the cornea by continually pumping water from the cornea into the anterior chamber of the eye.

The effects of exogenous HGF, KGF and EGF on the proliferation of cultured human corneal epithelial, stroma fibroblast and endothelial cells were compared. In each case, first passage cells from donors less than one year of age were plated in culture plates. Corneal epithelial cells, stroma fibroblast and corneal endothelial cells were plated in the wells for two days in an appropriate medium without KGF or HGF. The various growth factors were added individually and after five days of incubation, cells were trypsinized to complete dissociation and the number of cells in each well determined. The results showed that HGF and KGF significantly stimulated the in vitro proliferation of corneal epithelial cells and corneal endothelial cells. For both epithelial and endothelial cells, HGF or KGF significantly stimulated proliferation at a lower concentration than EGF. Moreover, HGF or KGF required a lower concentration than EGF to produce significant stimulation (see FIGS. 5–8). All three factors, HGF, KGF, or EGF, exhibited a decreased endothelial cell stimulatory effect at concentrations greater than about 50 ng/ml. This discovery indicated that corneal cells were stimulated by concentrations of about 1 to about 50 ng/ml but that at higher concentrations, inhibitory effects occurred.

The following examples illustrate the practice of the present invention and are not intended to be limiting. It will be recognized that numerous clinical applications of the keratinocyte and hepatocyte growth factors compositions are indicated, including in vivo and in vitro use, as mentioned previously herein.

The examples show that keratinocyte growth factor (KGF) and hepatoctye growth factor (HGF) are unexpectedly beneficial in corneal endothelial and epithelial cell wound healing and stimulate corneal cell proliferation at lower concentrations than EGF.

Materials

Corneal epithelial, stromal fibroblast, and endothelial cultures were prepared as described (Wilson and Loyd, 1991; Wilson, et al., 1992).

EXAMPLE 1

Detection of hepatocyte growth factor mRNA in corneal epithelial cells has not been previously reported, although it has been detected in vascular endothelial cells and Kupffer cells in the liver (Attisano, et al., 1992). The following experiment confirms the presence of HGF, KGF and their respective receptors in corneal endothelial and epithelial cells.

HGF, KGF, HGF Receptor, KGF Receptor and FGF Receptor-2 mRNA in Human Corneal Cells Human corneas stored for less than 96 hours in Optisol (Chiron Ophthalmics, Irvine, Calif.) were obtained from eye banks. Corneas were of transplant quality but were excluded from clinical use because of non-ocular exclusion criteria. Donors varied in age from term to 20 years of age, but all primary corneal endothelial cell cultures were derived from infant donors less than 6 months of age.

Senescent primary endothelial cell cultures were maintained without passage for 3 months until the majority of cells had the large, irregular, vacuolated, and sometimes multinucleated morphology characteristic of senescent corneal endothelial cells. Transfected endothelial cells 1, 2, and 3 were from three independent strains of cells transfected with the SV40 large T antigen coding plasmid $pSV_3$-neo. These cell strains were at passage 10, 25, and 21, respectively, with all passages after transfection being performed at a 1:2 split. Fetal calf serum and other reagents used for tissue culture were obtained from JRH Biosciences (Lanexa, Kans.). Anti-cytokeratin antibody immunofluorescence studies demonstrated that cultures of corneal epithelial cells (positive staining) prepared by these methods are pure cultures (Niederkorn, et al., 1990).

Normal human corneal epithelium was obtained for ex vivo studies by scraping the central cornea with a Paton spatula at the time of epikeratophakia or penetrating keratoplasty for an anterior stromal scar (Wilson, et al., 1992). Ex vivo corneal endothelium was obtained from the recipient button removed at the time of penetrating keratoplasty for an anterior stromal scar. Ex vivo tissues were immediately transferred into guanidinium thiocyanate (GTC) solution and used for RNA isolation (Wilson, et al., 1992). The research followed the tenets of the Declaration of Helsinki: informed consent was obtained from each patient prior to surgery after the nature and the possible consequences of the study were explained, and the research project was approved by the Investigational Review Board at the University of Texas Southwestern Medical Center (Dallas, Tex.).

Total cellular RNA and complementary DNA (cDNA) was prepared from 25 $cm^2$ flasks of near confluent cells using oligo dT primer (Wilson, et al., 1992) except that all cDNA reactions were prepared with 10 μg of total cellular RNA per 100 μl reaction. All of the RNA isolated from an ex vivo endothelial or epithelial specimen was included in a 70 μl cDNA synthesis (Wilson, et al., 1992) Mock cDNA samples were prepared using identical methods and reagents but no tissue was added to the RNA preparation.

The PCR primers that were used to amplify the cDNA sequences for beta actin, hepatocyte growth factor, hepatocyte growth factor receptor, keratinocyte growth factor, keratinocyte growth factor receptor, and FGF receptor-2 are described in Table 1. Beta actin served as an internal control for the efficiency of RNA isolation and cDNA synthesis in each sample. For the known genomic sequences, primer pairs were designed so that amplification of contaminating genomic DNA sequences would produce PCR products that were larger than PCR products amplified from cDNA (Table 1). The software program Oligos (National Biosciences, Inc., Plymouth, Minn.) was used to design PCR primers that were optimal and that would amplify at similar temperatures and magnesium concentrations. In addition, all primers and probes were compared to the Genebank and EMBL nucleic acid sequence libraries using the Intelligenetics Suite (Intelligenetics, Inc., Mountain View, Calif.) program to insure that they would not hybridize to any other known nucleic acid sequences under the conditions used. All PCR primers, except those for beta actin, were designed as part of the present invention using published nucleic acid sequences (Table 1). KGF PCR primers were synthesized 5' to 3' with a CTCCTCCTC clamp, a NotI site (GCGGCCGC) and the KGF sequence to facilitate cloning into vectors that require restriction digestion. Restriction sites were eliminated and the clamp was reduced to CTC on other primers with use of the TA Cloning System (Invitrogen, San Diego, Calif.) that does not require restriction digestion of the amplified product for cloning. All oligonucleotides were synthesized by Oligos etc. (Guilford, Conn.).

TABLE 1

Expected sizes of PCR amplification products with each primer pair.

| MODULATOR | SIZE | REFERENCES | UPSTREAM PRIMER | DOWNSTREAM PRIMER | PROBE |
|---|---|---|---|---|---|
| Beta actin | 350/790 | Mivechi et al. | 1628–1650 [GAAGTCCAGGGCGACGTAGCAC] | IC 2379–2400 [GAAGTCCAGGGCGACGTAGCAC] | None |
| HGF | 384/* | Ng S—Y et al. Nakamura et al. | 976–999 [AGTACTGTGCAATTAAAACATGCG] | IC 1333–1353 [TTGTTTGGGATAAGTTGCCCA] | IC 1015–1044 [CAGTTGTTTCCATAGGAACATCAGTATCAT] |
| HGF receptor | 342/unk | Miyazawa et al. Park et al. | 3993–4013 [TTGGTCCTTTGGCGTCGTCCTC] | IC 4308–4328 [CTCATCATCAGCGTTATCTTC] | IC 4134–4164 [CTTTAGGGTGCCAGCATTTTAGCATTACTT] |
| KGF | 669/un | Finch et al. | 1488–1509 [GCCAACTAACTATGGAAAATG] | IC 2128–2150 [TTCCAGGATTTGCTGGCCCAAGT] | IC 1910–1929 [CCATAGGAAAAAGCATGATTATTTGTGGG] |
| KGF receptor | 178/1200 | Miki et al. | 3–23† [GGATCAAAGCACGTGGAAAAGA] | IC 83–103¶ [GCCCTATATAATTGGAGACCT] | IC 30–60¶ [GCCTCGGTCACATTGAACAGAGCCAGCACT] |
| FGF recept-2 | 205/2400 | Miki et al. | 3–23† [GGATCAAAGCACGTGGAAAAGA] | IC 110–130§ [ACCATGCAGAGTGAAAGGATA] | IC 30–59§ [GTTACATTCCGAATATAGAGAACCTCAATC] |

Size indicates the expected size of the amplified sequences from cDNA or genomic DNA, including 5' clamps included on primers for growth factors, cytokines, and receptors. Unknown indicates that the genomic sequence has not been reported. The references are those for the cDNA/genomic sequences. IC indicates that the primer or probe was the inverse complement of the specified nucleotides from the indicated reference. All primers and probes were designed by the authors except those for beta actin that were obtained from the listed reference. All sequences are the actual primer and probe sequences from 5' to 3', but CTC clamps that were included at the 5' end of primers are not shown. The size of the beta actin fragment does not correspond to the nucleotide numbers since the referenced sequence is for genomic DNA and includes an intron that is excised during RNA processing.
†, ¶, and § indicate exons U, K, and B, respectively, of the provided reference. Note that KGF receptor and FGF receptor-2 sequences are amplified using the same upstream primer.
*Complete HGF genomic organization has not been reported, but the upstream primer is in exon 7 and the downstream primer is in exon 10 and, therefore, genomic amplification from these primers would be much larger than 384 base pairs. The beta actin upstream and downstream primers are both represented by SEQ ID NO:1. Starting with the HGF upstream primer, and reading from left to right until the KGF receptor, the various primers and probes are represented by SEQ. ID. NO:2 through SEQ ID NO:13, respectively. The FGF recept-2 upstream primer, downstream primer and probe are represented by SEQ ID NO:14 and SEQ ID NO:15, respectively.

PCR amplification of each sequence was performed with 5 μl of cDNA sample from cell cultures or 10 μl of cDNA from ex vivo samples in a total volume of 100 μl using 2 units of Taq polymerase (Promega, Madison, Wis.) and 1.5 mM magnesium (Wilson, et al., 1992). All of the test samples were amplified simultaneously with a particular primer pair and a master mix containing all of the components in the PCR reaction, except the target cDNA or water negative control, was used to prepare the individual reactions. All PCR reactions were prepared using the hot start method (D'Aquila, et al., 1991) in which the target and PCR master mix solution were brought to 80° C. prior to mixing and were maintained at that temperature for several minutes before beginning the PCR cycle. Control reactions without template were included with each amplification for each pair of primers. Programmable temperature cycling (Ericomp, Inc., La Jolla, Calif.) was performed with the following cycle profile: Denaturation 4 minutes at 94° C., followed by 40 cycles of annealing 3 seconds at 55° C., extension 1 minute at 72° C., and denaturation 30 seconds at 94° C. Horizontal 1.5% agarose (US Biochemical Corp, Cleveland, Ohio) gel electrophoresis was performed by a previously described technique (Wilson, et al., 1992). Twenty seven μl of each PCR product was evaluated in a slot on a 120 ml gel. One hundred base pair DNA ladder or φX174/Hae III fragments (Bethesda Research Laboratories, Gaithersburg, Md.) were used as molecular size standards. Unless otherwise specified, all reagents were obtained from Sigma (St Louis, Mo.).

The hot blot method was used to demonstrate that each of the amplified sequences was specific. The probes used to detect the amplified sequences (Table 1) were designed to be complementary to an internal sequence in the amplified region that did not overlap with the PCR primer sequences. Size markers were included on each hot blot gel and were photographed with a ruler aligned with the markers to allow calculation of the sizes of the products detected on the auto radiograms.

Figure 1B:
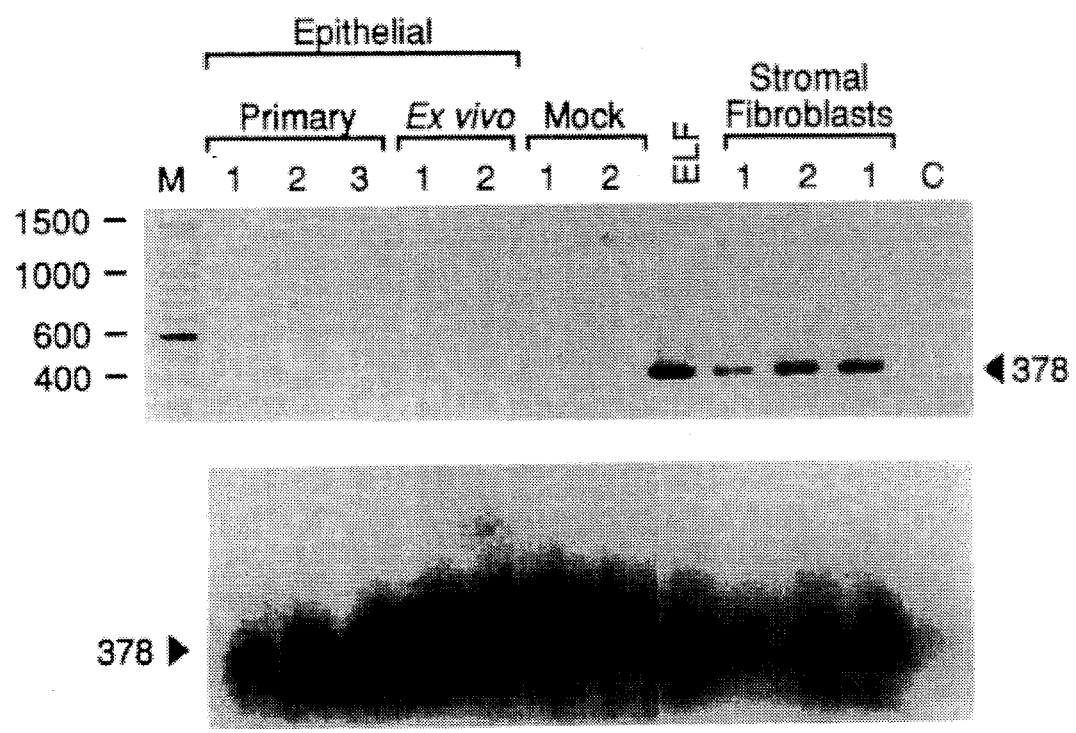

FIG. 1 shows that hepatocyte growth factor mRNA PCR amplifications were strongest in stromal fibroblasts and embryonic lung fibroblasts. Hepatocyte growth factor was also readily detectable in proliferative primary, senescent primary, and transfected corneal endothelial cells. Hepatocyte growth factor mRNA was present in corneal epithelial cells in much smaller amounts compared to stromal fibroblasts and corneal endothelial cells based on visual inspection of the ethidium bromide stained agarose gels in FIG. 1. Hepatocyte growth factor mRNA was present in variable amounts in all three major cell types of the cornea. There is a marked difference in the amplified signal in the stromal fibroblast and endothelial cell samples compared to the corneal epithelial samples. These data demonstrated that human corneal epithelial cells and corneal endothelial cells produced messenger RNA coding for hepatocyte growth factor.

Figure 2A:
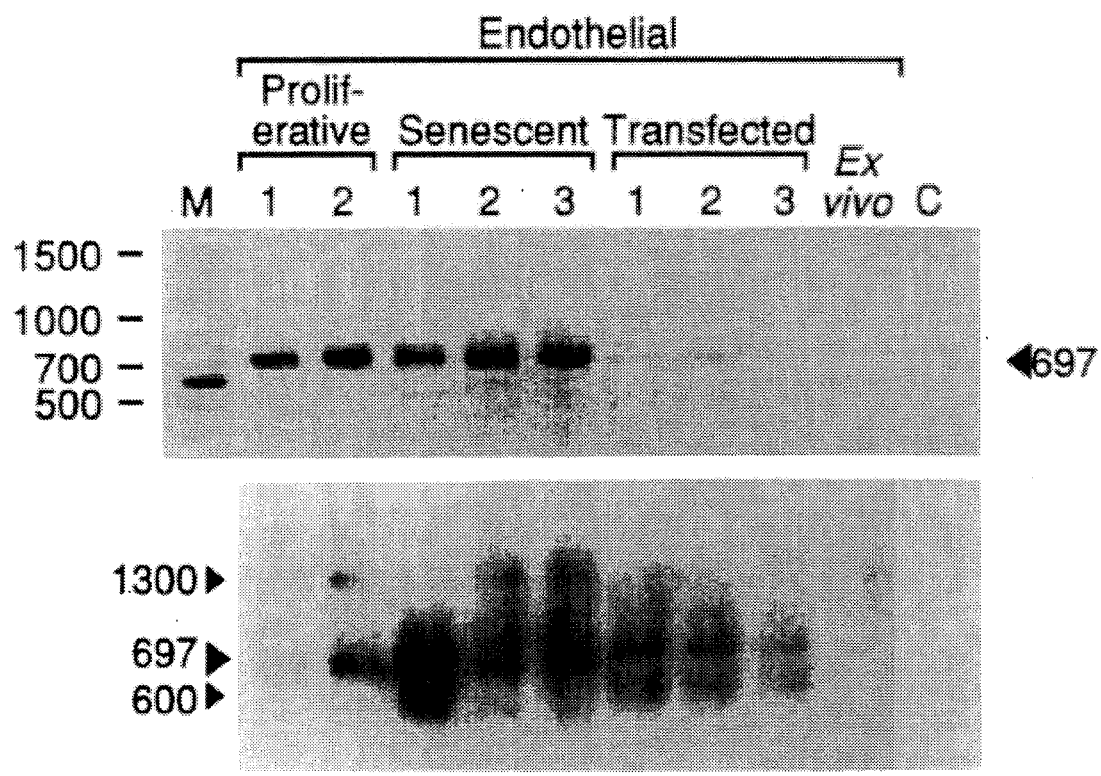
FIGS. 2A and 2B show keratinocyte growth factor PCR-amplified products that were amplified using the hot start method from the cDNA samples generated from human cells.
Figure 2B:
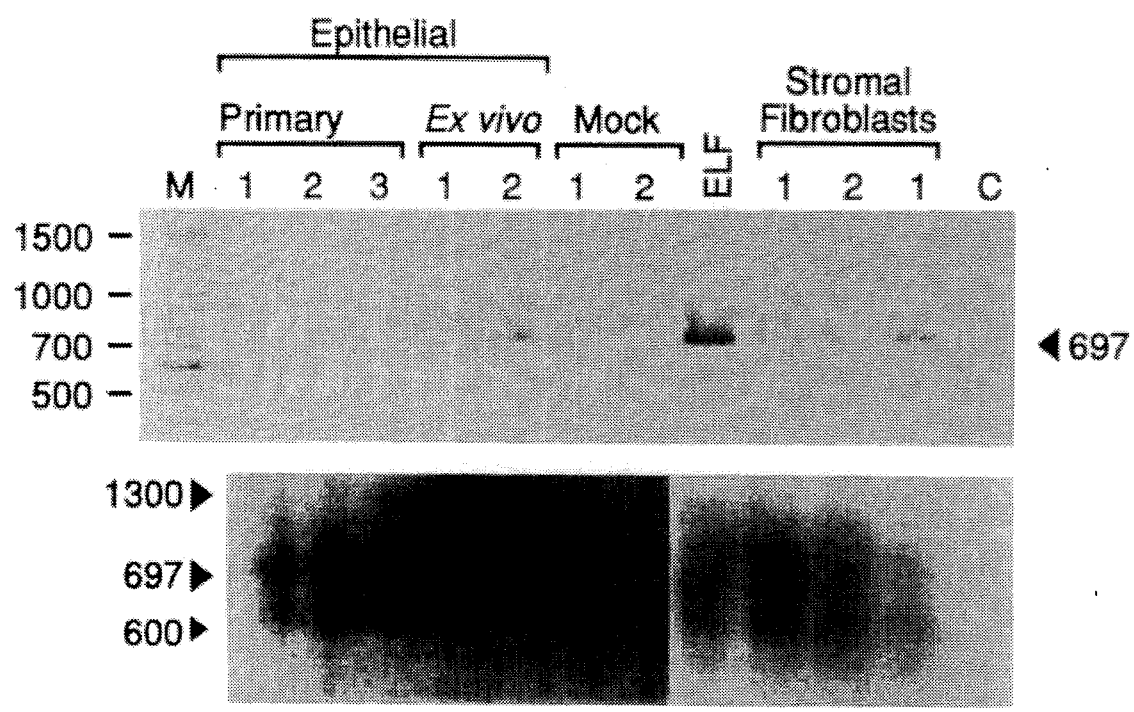

FIG. 2 shows that the 697 base pair KGF specific amplification product was detectable in each of the cell types evaluated. This amplification product was prominent in the proliferative and senescent corneal endothelial cells and stromal fibroblasts, but was also detectable in transfected corneal endothelial cells and primary corneal epithelial cells. The hot blots in FIG. 4 demonstrated that the 697 base pair amplification product was specific for KGF and that the product was detectable in corneal epithelial cells. In addition, other KGF specific amplification products at approximately 600 and 1300 base pairs were detected in some of the cells. The latter products could not be detected on the ethidium bromide stained gels. The approximately 600 base pair amplification product was detectable in each of the cell types of the cornea, but appeared to be slightly larger in the transfected endothelial cell. The 1300 base pair amplification product was detectable in only one of the epithelial samples, ex vivo sample 1 (FIG. 2B). While Langerhan's cells and possibly other cell types present in the ex vivo corneal epithelial tissue may have contributed to the KGF signal, it is likely that the different sized products were amplifications from different keratinoctye growth factor-specific mRNA transcripts in all three major cell types of the cornea, albeit at lower levels in the corneal epithelial cells.

Figure 3A:
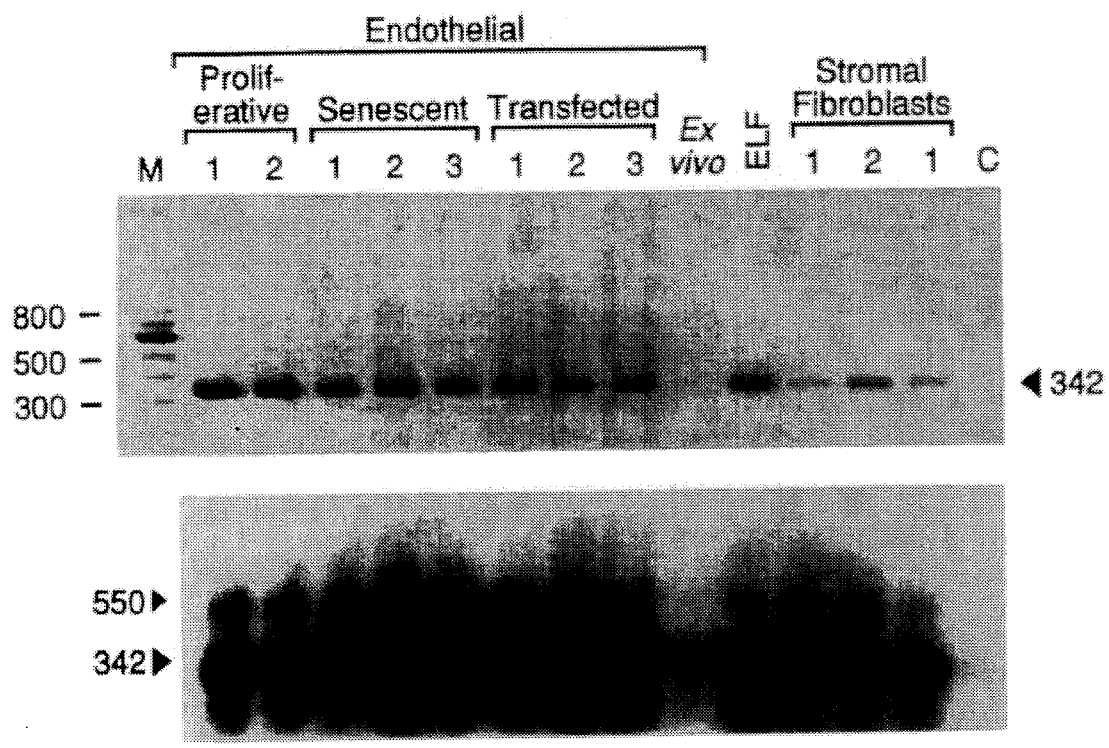
FIGS. 3A and 3B shows hepatocyte growth factor receptor PCR products amplified in the same experiment using the hot start method from the cDNA samples generated from human cells.
Figure 3B:
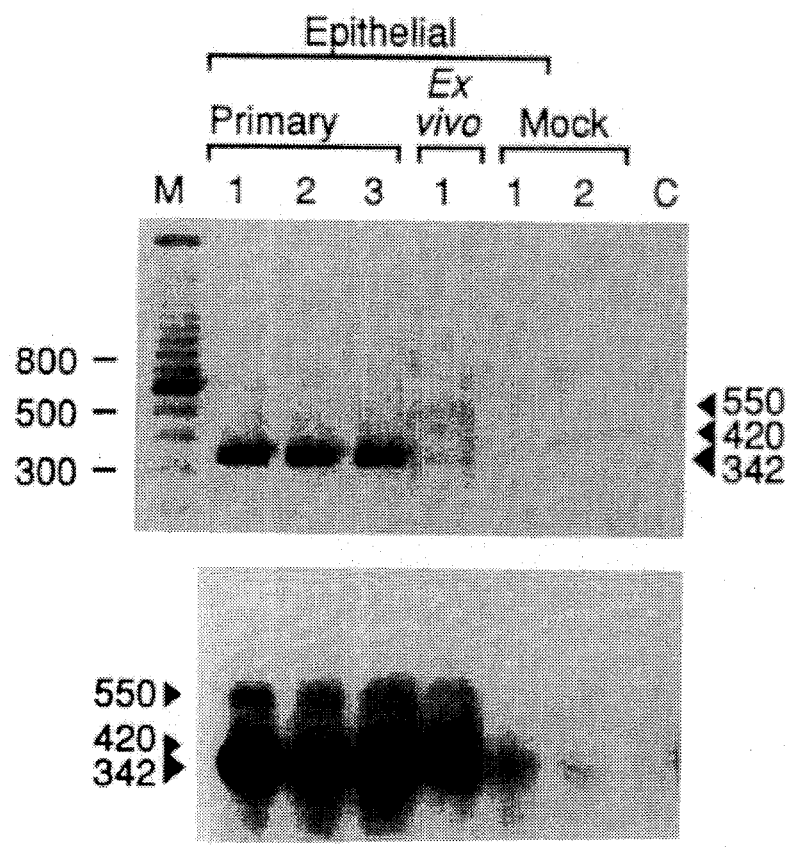

FIG. 3 shows that amplification products of the expected size for the hepatocyte growth factor receptor (342 base pairs) were detectable in each of the cell types evaluated. The hot blots in FIG. 3 show that the amplification product of the expected size was specific for hepatocyte growth factor receptor. In addition, a specific alternative PCR product approximately 550 base pairs in size was detected in each cell type. An additional band at approximately 420 base pairs was present in the ex vivo epithelium sample on the ethidium bromide stained gel and the hot blot (FIG. 3B). This 420 base pair product may represent a PCR amplification product that was derived from an alternative hepatocyte growth factor receptor mRNA. The major amplification product on the ethidium bromide stained agarose gel was 342 base pairs in size. Hot blots of the same samples demonstrate the specificity of the 342 base pair PCR product and revealed an amplified product identified by the hepatocyte growth factor receptor probe in some samples at 550 base pairs. An amplified product in ex vivo epithelial sample 1 at approximately 420 base pairs was also detected on the hot blot. The data represented in FIG. 3 demonstrate that human corneal epithelial cells and corneal endothelial cells produce messenger RNA coding for hepatocyte growth factor receptor.

Figure 4A:
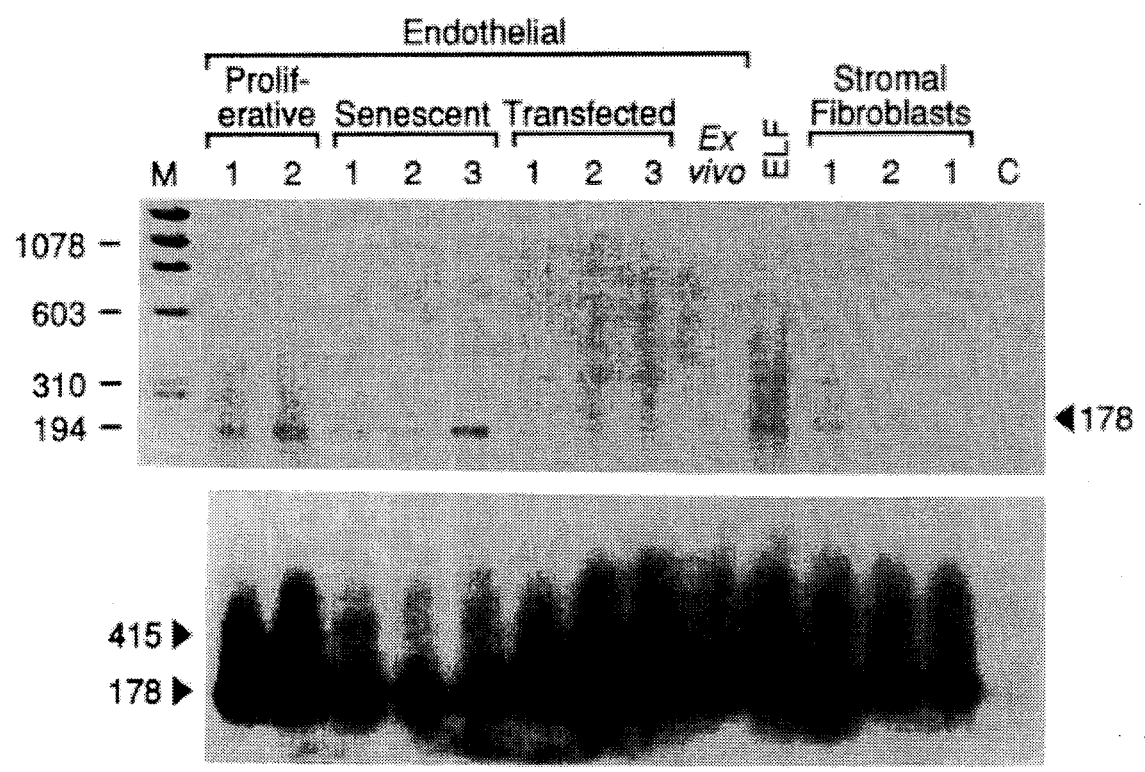
FIGS. 4A and 4B shows keratinocyte growth factor receptor PCR products amplified in the same experiment using the hot start method from the cDNA samples generated from human cells.
Figure 4B:
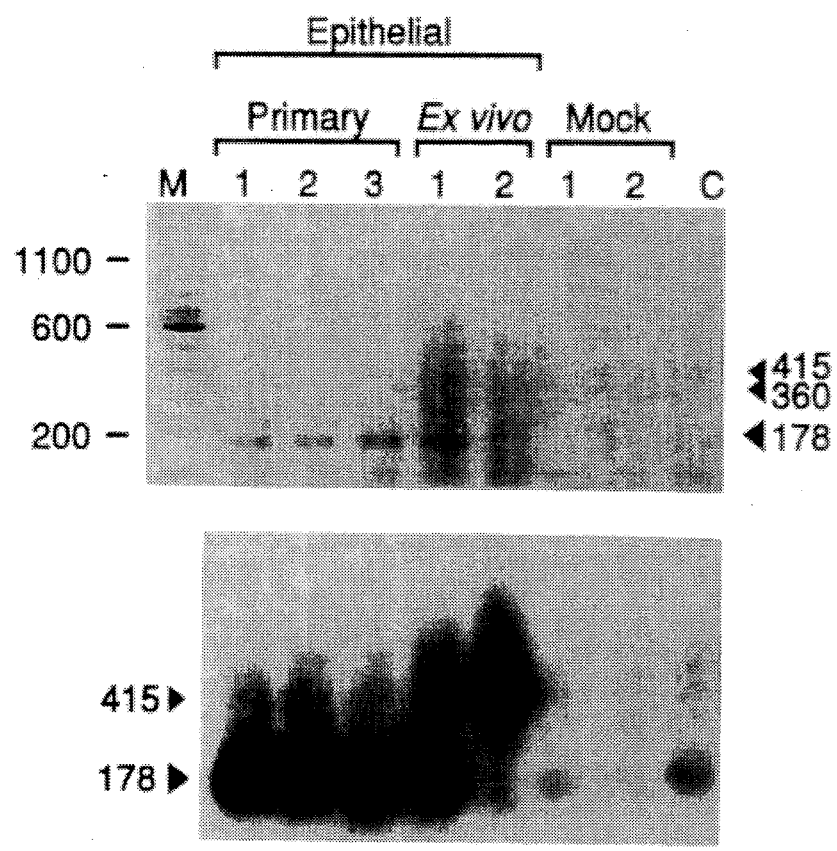

Keratinocyte growth factor receptor and FGF receptor-2 are derived by alternative mRNA splicing from the same gene (bek), with keratinocyte growth factor receptor having a high affinity for keratinocyte growth factor and acidic FGF and FGF receptor-2 having a high affinity for basic and acidic FGF (Miki, et al., Specific amplification products of the expected size for the keratinocyte growth factor receptor (178 base pairs) were also detectable in each of the cell types evaluated (FIG. 4). The corresponding band in ex vivo epithelial cell sample 2 was shifted to a slightly larger size relative to the adjacent bands (FIG. 6B). Also, in the ex vivo epithelium sample, two additional bands were noted at approximately 415 and 360 base pairs. Hot blots of the same samples demonstrated the specificity of the 178 base pair PCR product and revealed the 415 base pair amplified product in several samples. The latter band was prominent in ex vivo epithelium sample 2. The shifted lower band at approximately 200 base pairs and the 360 base pair band in ex vivo epithelium sample 2 (FIG. 4) were not identified on the hot blot. The 415 base pair PCR products were not large enough to represent amplifications from genomic DNA (Table 1) and, therefore, most likely represent amplifications from precursor RNAs or alternatively-spliced mRNA transcripts.

EXAMPLE 2

The work described in the following example on corneal epithelial and corneal endothelial cells shows that hepatocyte growth factor and keratinocyte growth factor can be used to regulate corneal epithelial and endothelial wound healing or to improve the viability of corneal endothelial cells during corneal preservation.

Effects of KGF and HGF on Corneal Epithelial and Endothelial Cell Proliferation

All experiments on the effects of exogenous growth factors on proliferation were performed with first passage corneal epithelial and endothelial cells. Proliferation experiments were performed with Costar (Cambridge, Mass.) 12-well plates. Plates used for epithelial cell experiments were precoated with poly-D-lysine (Sigma, St Louis, Mo.) at 0.1 mg/ml in sterile water, washed twice with sterile water, coated with fibronectin (Sigma) at 50 µg/ml in HBSS, and washed with sterile medium (Marchese, et al., 1990). Plates used for stromal fibroblasts and endothelial cells were not precoated. Epithelial cell proliferation experiments were performed in Keratinocyte Defined Medium (KDM, modified MCDB 153, 5 µg/ml insulin, 0.5 µg/ml hydrocortisone, and 0.15 mM $Ca^{2+}$, and 0.1 ng/ml human epidermal growth factor (Clonetics, San Diego, Calif.).

Epithelial cells were plated for the first two days in KDM with epidermal growth factor (since cells initially plated in KDM without epidermal growth factor did not adhere well). Prior to the addition of test growth factors, epithelial cells were washed twice with KDM without epidermal growth factor and 1 ml of KDM without epidermal growth factor was added per well. Stromal fibroblast proliferation experiments were performed in Fibroblast Basal Medium (FBM, Modified MCDB 202 with 5 mg/ml insulin, Clonetics).

Corneal endothelial cell proliferation experiments were performed in medium with 0.5% fetal bovine serum as the only serum source. All growth factors were obtained commercially (human hepatocyte growth factor, #904792, Collaborative Biomedical Products, Bedford, Mass.; human keratinocyte growth factor, H-1086, Bachem, Philadelphia, Pa.; human epidermal growth factor, 920126, Collaborative Biomedical Products; human basic FGF, CC-4065, Clonetics, San Diego, Calif.). Stock growth factors were aliquoted into siliconized microtubes and stored at −80° C. so that they were thawed only one additional time prior to use.

Epithelial, stromal fibroblast, and endothelial cells were plated at 10,000 cells per well in all experiments. For each experiment, cells were plated in 1.0 ml of the appropriate medium per well and incubated for 2 days at 37° C. Cells were washed with the appropriate medium and 1.0 ml of fresh medium was added. Growth factors were then added to each well. Growth factors were diluted at the time of addition in sterile PBS with 0.2% gelatin so that 5 µl of additional volume was added to each well to give the final concentration. In each growth factor experiment, each concentration of growth factor(s) was tested in 6 wells. Twelve control wells were included to which 5 µl of PBS with 0.2% gelatin were added. Hepatocyte growth factor, keratinocyte growth factor, and epidermal growth factor were tested at 50, 25, 10, 5, 2.5, and 1 ng/ml. As a positive control, basic FGF was tested at 25 ng/ml in the stromal fibroblast experiments. In the combined growth factor experiment for corneal epithelial cells, each growth factor was tested at 10 ng/ml, individually or in combination, in each well. Cells were incubated an additional 5 days at 37° C after the addition of growth factors. Each well was then washed twice with 1.0 ml of PBS, trypsinized to complete dissociation with 0.5 ml of 0.25% trypsin (approximately 10 minutes), and the cells in each well transferred quantitatively to a Coulter vial with Coulter fluid to give a final volume of 10 ml per well. The total number of cells for each well was determined from the average of 3 measurements, minus the background, determined with a Coulter counter (Model Zf, Hialeah, Fla.). Errors were expressed as the standard error of the mean. Statistical comparisons were performed with the Newman-Keuls nonparametric multiple comparison test. A Z value less than 0.05 was considered statistically significant.

Exogenous hepatocyte growth factor and keratinocyte growth factor significantly stimulated the proliferation of first passage corneal epithelial and endothelial cells from young human donors in a dose response manner (FIGS. 5, 6, 7 and 8) up to about 50 ng/ml. EGF showed stimulation up to about 25 ng/ml. Generally, HGF and KGF stimulated proliferation in both cell types at lower concentrations than did EGF. The stimulatory effect of HGF, KGF and EGF was not present at higher concentrations. Combinations of HGF, KGF and EGF did not increase corneal epithelial cell proliferation. When the three growth factors were combined at concentrations of 10 ng/ml each, however, there was no longer a significant effect on proliferation. Corneal epithelial cell proliferation was increased by HGF and KGF in defined serum-free medium with 0.15 mM $Ca^{2+}$.

Hepatocyte growth factor, however, stimulated corneal cell proliferation at 1.8 mM $Ca^{2+}$, but supressed proliferation at 0.1 mM $Ca^{2+}$(data not shown).

Figure 5:
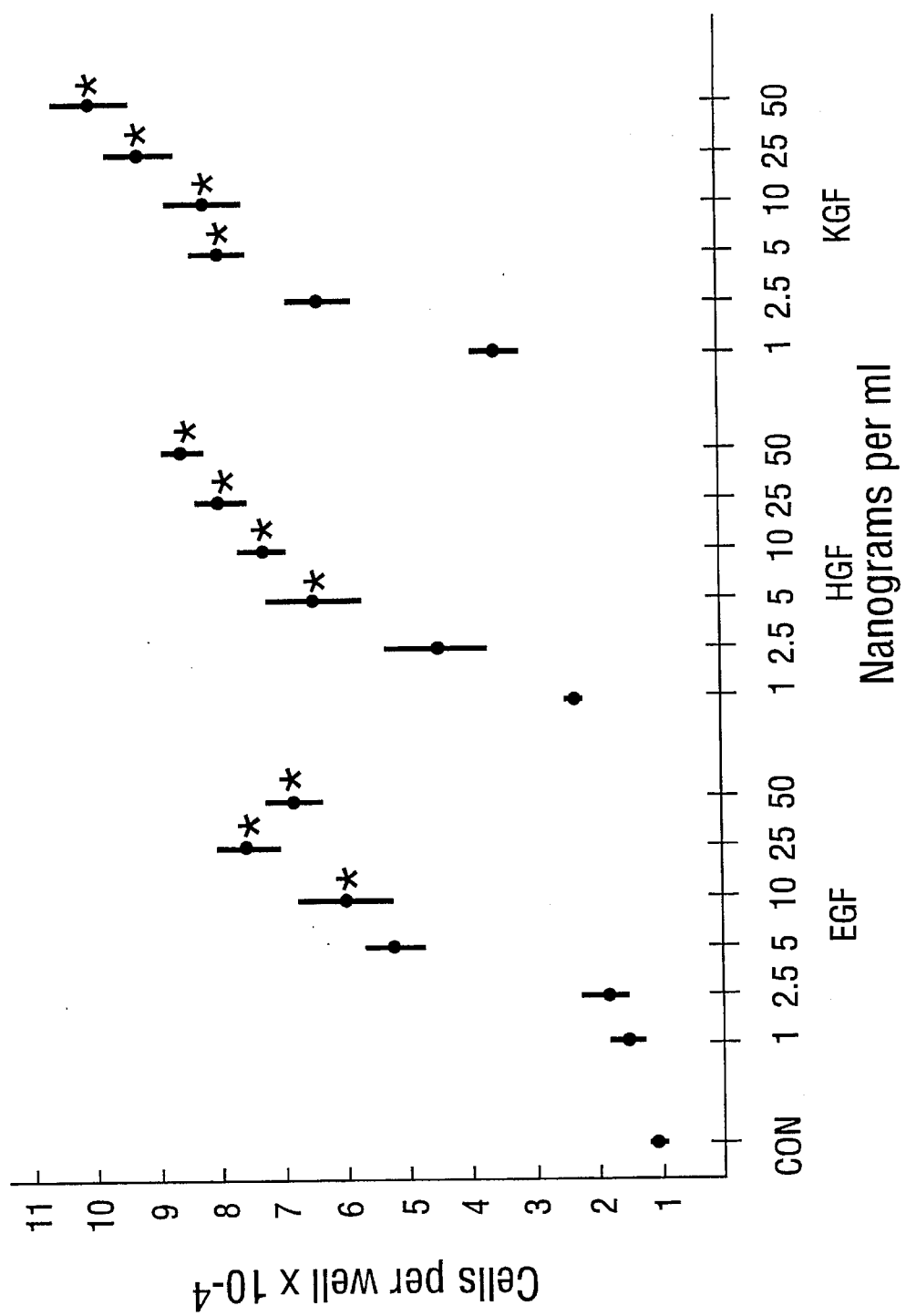
FIG. 5 shows mitogenic effects of epidermal growth factor, hepatocyte growth factor, and keratinocyte growth factor on the first passage human corneal epithelial cells (experiment 1). Data are presented as the mean±the standard error of the mean for the 12 control wells and the 6 wells for each growth factor concentration in each experiment. Asterisks (*) indicate that the effect was statistically significant compared to the control group.
Figure 6:
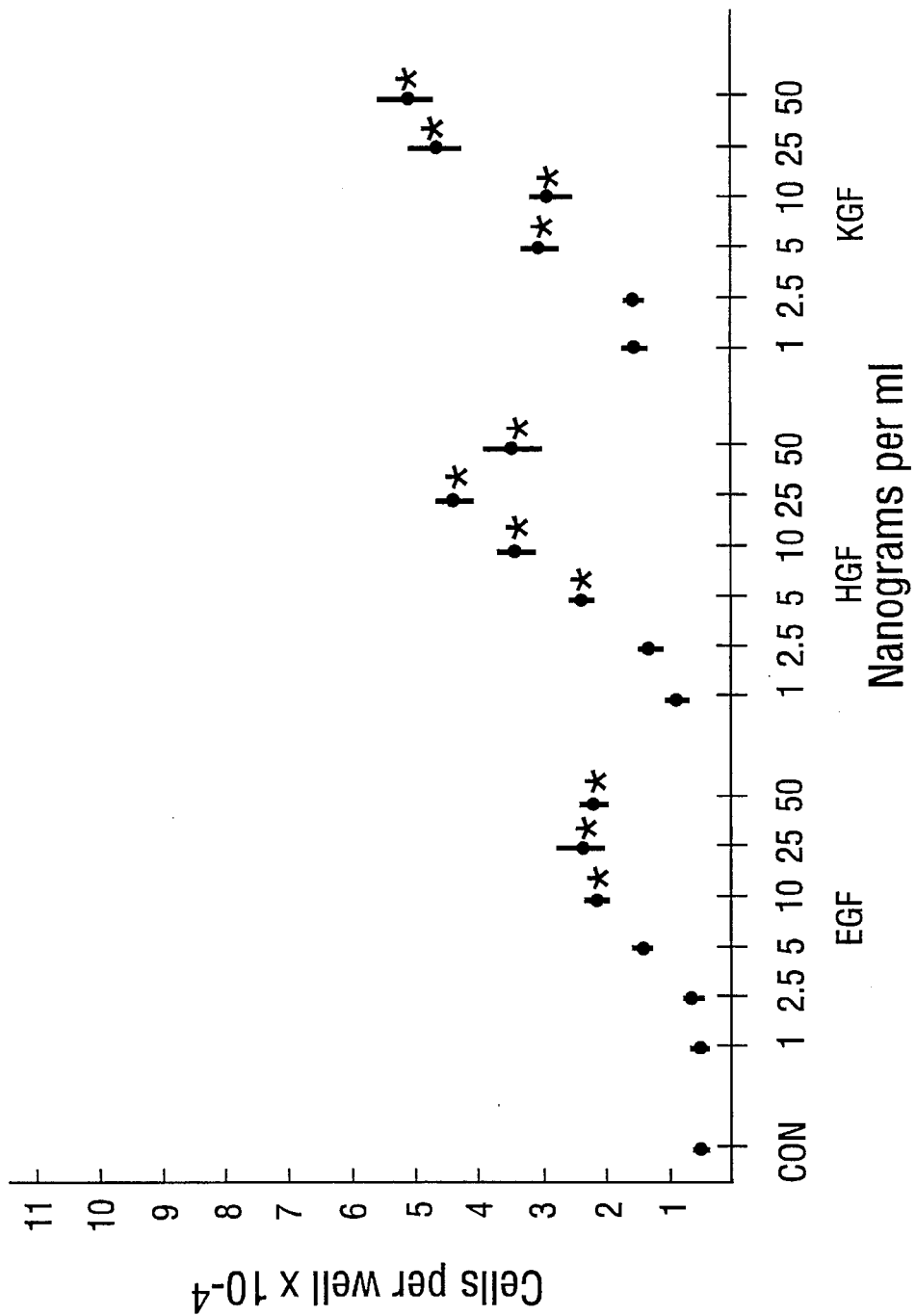
FIG. 6 shows mitogenic effects of epidermal growth factor, hepatocyte growth factor, and keratinocyte growth factor on the first passage human corneal epithelial cells (experiment 2). Data are presented as the mean±the standard error of the mean for the 12 control wells and the 6 wells for each growth factor concentration in each experiment. Asterisks (*) indicate that the effect was statistically significant compared to the control group.
Figure 7:
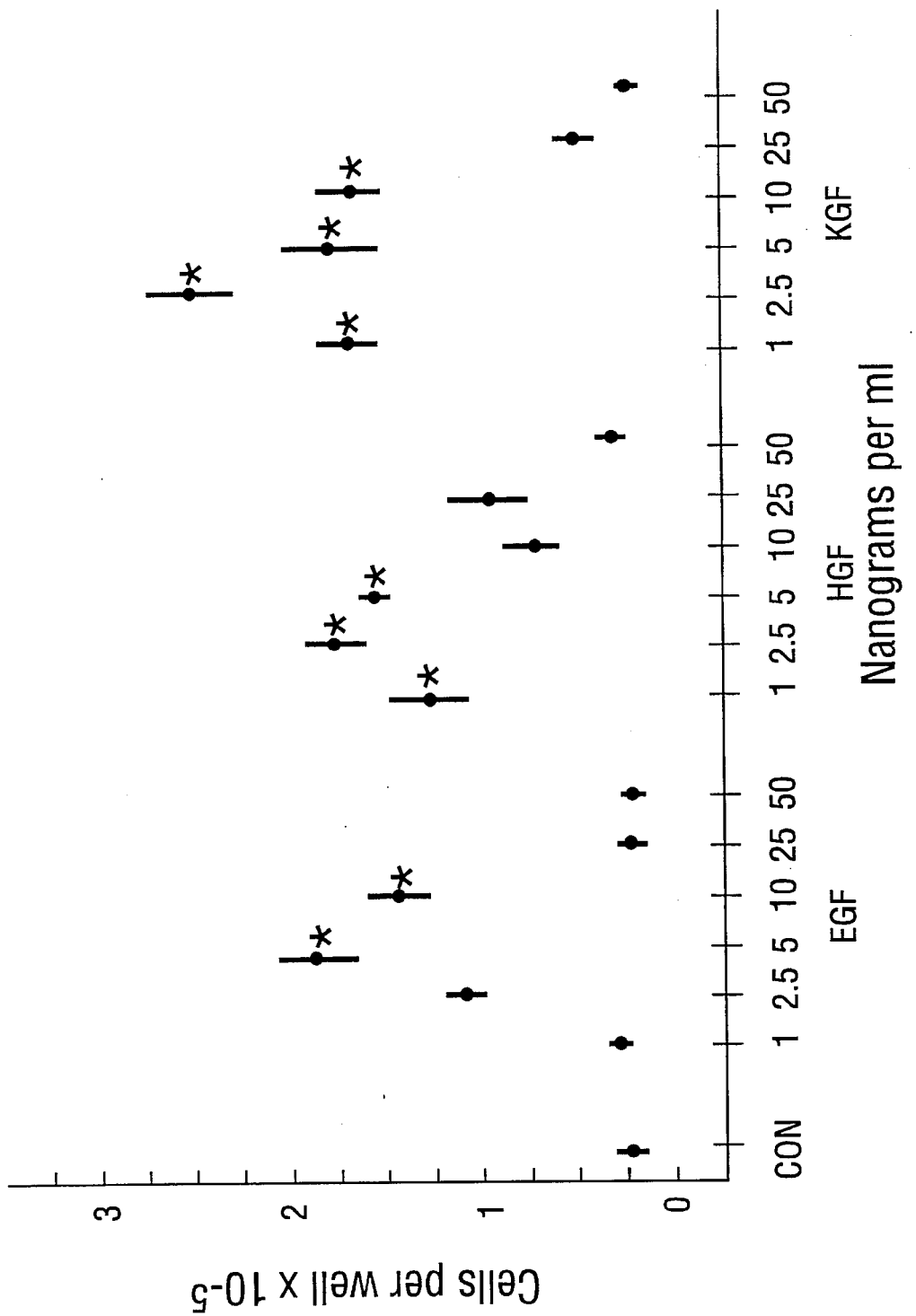
FIG. 7 shows mitogenic effects of epidermal growth factor, hepatocyte growth factor, and keratinocyte growth factor on the first passage human corneal endothelial cells (experiment 1). Data are presented as the mean±the standard error of the mean for the 12 control wells and the 6 wells for each growth factor concentration in each experiment. Asterisks (*) indicate that the effect was statistically significant compared to the control group.
Figure 8:
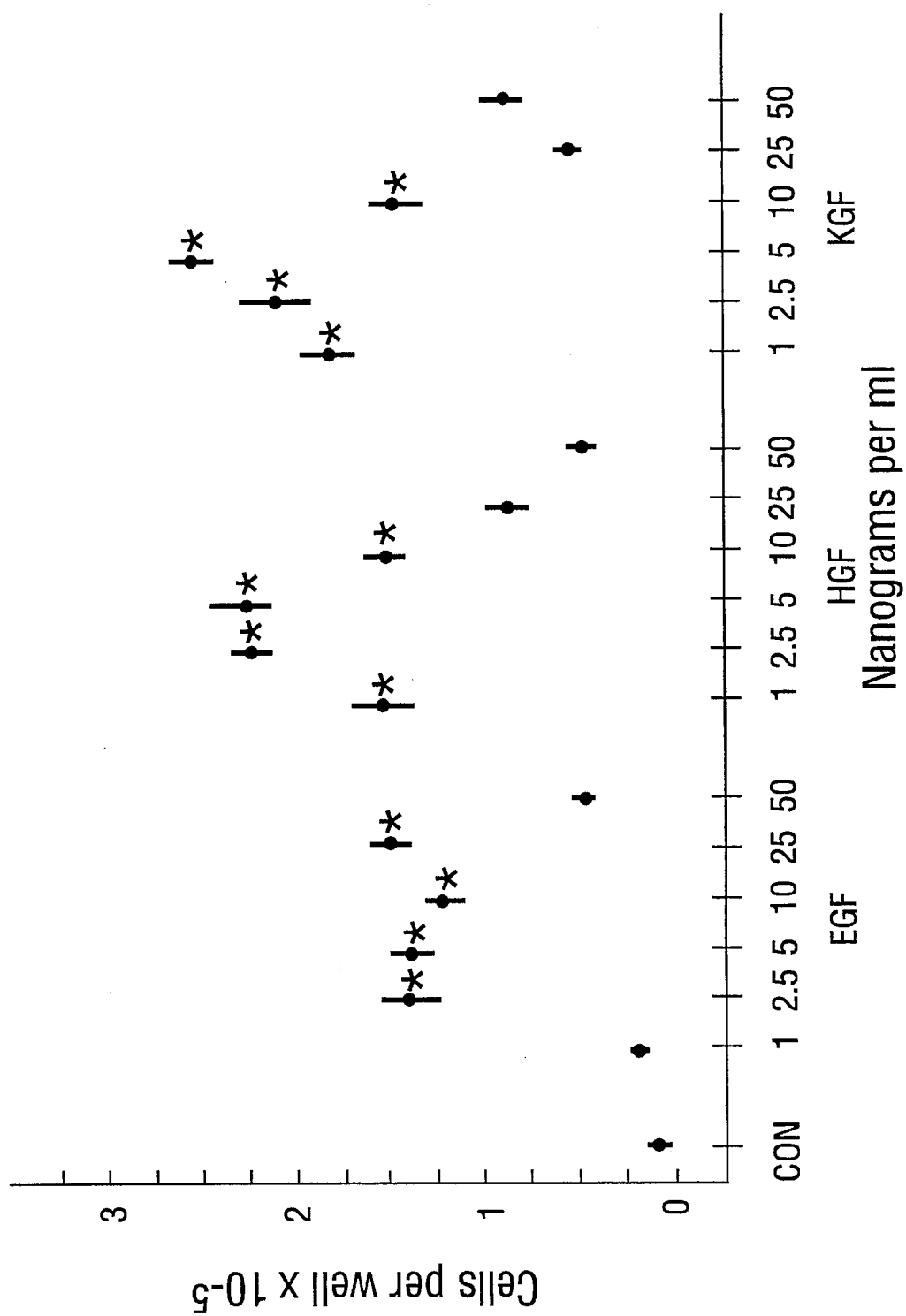
FIG. 8 shows mitogenic effects of epidermal growth factor, hepatocyte growth factor, and keratinocyte growth factor on the first passage human corneal endothelial cells (experiment 2). Data are presented as the mean±the standard error of the mean for the 12 control wells and the 6 wells for each growth factor concentration in each experiment. Asterisks (*) indicate that the effect was statistically significant compared to the control group.

Corneal epithelial cell proliferation was stimulated by either HGF or KGF at concentrations up to about 50 ng/ml. EGF stimulation dropped above a concentration of about 25 ng/ml. At 1 ng/ml, EGF had little or no effect on corneal epithelial stimulation, but there was noticeable stimulation by either HGF or KGF at this concentration. At 2.5 ng/ml, both KGF and HGF showed significantly greater stimulatory effects than EGF (see FIG. 5 and FIG. 6). Maximal corneal epithelial cell stimulation by HGF or KGF was in the range of about 50 ng/ml, although maximal stimulation for KGF may have been somewhat higher as indicated in FIG. 5. Doses higher than 50 ng/ml were not tested.

Corneal endothelial proliferation was significantly stimulated by HGF or KGF at 1 ng/ml. Virtually no stimulation was observed with EGF at this concentration (see FIG. 7 and FIG. 8). Maximal stimulation for either HGF or KGF was at a concentration of about 2.5 ng/ml.

Increased proliferation of corneal epithelial and endothelial cells in response to exogenous hepatocyte growth factor and keratinocyte growth factor indicates a function in controlling proliferation in these cell types. HGF and KGF also are useful for storing corneas in preservation medium prior to corneal transplant. These factors appear to have a trophic effect on corneal cell stimulation, indicating that viability of corneal epithelial cells and endothelial cells will be improved.

REFERENCES

The references listed below are incorporated herein by reference to the extent they supplement, explain, provide a background for or teach methodology, techniques and/or compositions employed herein.

Attisano L., Wrana J. K., Cheifetz S., Massagu J. Novel activan receptors. Distinct genes and alternative mRNA splicing generate a repertoire of serine/threonine kinase receptors. Cell. 1992;68:97–108.

Bottaro D. P., Fleming T. P., Smith C. L., Burgess W. H., Chan A. M.-L., Aaronson S. A. Determination of ligand-binding specificity by alternative splicing: two distinct growth factor receptors encoded by a single gene. *Proc. Natl. Acad. Sci.* 1992;89:246–250.

Bottaro D. P., Rubin J. S., Faletto D. L., Chan A. M. L., Kmiecik T. E., Vande Woude G. F., and Aaronson S. A. Identification of the hepatocyte growth factor receptor as c-met proto-oncogene product. *Science.* 1991;251:802–804.

Bottaro D. P., Rubin J. S., Ron D., Finch P. W., Florio C., and Aaronson S. A. Characterization of the receptor for keratinocyte growth factor. *J. Biol. Chem.* 1990;265:12767–12770.

Brazzell R. K., Stern M. E., Aquavella J. V., Beuerman R. W., Baird L. Human recombinant epidermal growth factor in experimental corneal wound healing. Invest. O., *Pathalmol. Vis. Sci.* 1991;32:336–40.

Brogdon J. D., McLaughlin S. A., Brightman A. H., Helper L. C. Effect of epidermal growth factor on healing of corneal endothelial cells in cats. *Am. J. Vet. Res.* 1989;50:1237–43.

Chung J. H., Fagerholm P. Treatment of rabbit corneal alkali wounds with human epidermal growth factor. *Cornea.* 1989;8:122–8.

D'Aquila, Bechtel L., Videler J. A., Eron J., Gorczyca P., Kaplan J. C. Maximizing sensitivity and specificity of PCR by preamplification heating. *Nucleic Acid. Res.* 1991;19:3749.

Finch P. W., Rubin J. S., Miki T., Ron D., Aaronson S. A. Human KGF is FGF-related with properties of a paracrine effector or epithelial cell growth. *Science.* 1989;245:752–755.

Gherardi E. and Stoker M. Hepatocytes and Scatter factor. *Nature.* 1990;346:228.

Gospodarowicz D., Mescher A. L., Brown K. D., Birdwell C. R. The role of fibroblast growth factor and epidermal growth factor in the proliferative response of the corneal and lens epithelium. *Exp. Eye. Res.* 1977;25:631–49.

Joyce N. C., Matkin E. D., Neufeld A. H. Corneal endothelial wound closure in vitro. Effects of epidermal growth factor and/or indomethacin. *Invest. Ophthalmol. Vis. Sci.* 1989;30:1548–59. corneal endothelial cells Junquero D., Modat G., Coquelet C., Bonne C. Retinoid-induced potentiation of epidermal growth factor mitogenic effect on corneal endothelial cells. *Cornea.* 1990;9:41–4.

Kandarakis A. S., Page C., Kaufman H. E. The effect of epidermal growth factor on epithelial healing after penetrating keratoplasty in human eyes. *Am. J. Ophthalmol.* 1984;98:411–5.

Kitazawa T., Kinoshita S., Fujita K., Araki K., and others. The mechanism of accelerated corneal epithelial healing by human epidermal growth factor. *Invest. Ophthalmol. Vis. Sci.* 1990;31:1773–81.

Laas J., Unpublished data, personal communication, Cleveland, Ohio, Chief investigator (Aug. 6,. 1992).

Marchese C., Rubin J., Ron D., Faggioni A., Torrisi M. R., Messina A., Frati L., and Aaronson S. A. Human keratinocyte growth factor activity on proliferation and differentiation of human keratinocytes: differentiation response distinguishes keratinocyte growth factor from epidermal growth factor family. *J. Cell. Physiology* 1990;144:326–332.

Matsumoto K., Hashimoto K., Yoshikawa K., and Nakamura T. Marked stimulation of growth and motility of human keratinocytes by hepatocyte growth factor. *Exp. Cell. Res.* 1991;196:114–120.

Miki T., Bottaro D. P., Fleming T. P., Smith C. L., Burgess W. H., Chan A. M.-L., Aaronson S. A. Determination of ligand-binding specificity by alternative splicing: two distinct growth factor receptors encoded by a single gene. *Proc. Natl. Acad. Sci.* 1992;89:246–250. Miki T., Mivechi N. F., Rosi J. J. Use of polymerase chain reaction to detect the expression of the Mr 70,000 heat shock genes in control or heat shock leukemic cells as correlated to their heat response. *Cancer Res.* 1990;50:2877.

Miyazawa K., Tsubouchi H., Naka D., Takahashi K., Okigaki M., Arakaki N., Nakayama H., Hirono S., Sakiyama O., Takahashi K., Gohda E., Daikuhara Y., Kitamura N. Molecular cloning and sequence analysis of cDNA for human hepatocyte growth factor. *Biochem. Biophys. Res. Commun.* 1989;163, 967–973.

Monteasano R., Matsumoto K., Nakamura T., and Orci L. Identification of a fibroblast-derived epithelial morphogen as hepatocyte growth factor. *Cell.* 1991;67:901–908.

Nakamura T., Nishizawa T., Hagiya M., Seki T., Shimonishi M., Sugimura A., Tashiro K., Shimizu S. Molecular cloning and expression of human hepatocyte growth factor. *Nature.* 1989;342:440–443.

Nayak S. K., Binder P. S. The growth of endothelium from human corneal rims in tissue culture. *Invest. Ophthalmol. Vis. Sci.* 1984;25:1213–6.

Neufeld A. H., Joyce N. C., and Jumblatt M. M. Composition for enhancing healing of corneal endothelial tissue Ng S.-Y., Gunning P., Eddy R., Ponte P., Leavitt J., Shows T., Kedes L. Evolution of the functional human beta-actin gene and its multi-pseudogene family: Conservation of noncoding regions and chromosomal dispersion of pseudogenes. *Mol. Cell. Biol.* 1985;5:2720.

Niederkorn J. Y., Meyer D. R., Ubelaker J. E., Martin J. H. Ultrastructural and immunohistological characterization of the SIRC corneal cell line. *In Vitro Cell. Der. Biol.* 1990;26:923.

Park M., Dean M., Kaul K., Braun M. J., Gonda M. A., Vande W. G. Sequence of MET protooncogene cDNA has features characteristic of the tyrosine kinase family of growth factor receptors. *Proc. Natl. Acad. Sci.* 1987;84:6379–6383.

Parker J. D., Burmer G. C. The oligomer extension "hot blot": A rapid alternative to Southern blots for analyzing polymerase chain reaction products. *Biotechniques.* 1991;10:94.

Prat M., Narsimhan R. P., Crepaldi T., Nicotra M. R., Natali P. G., Comoglio P. M. The receptor encoded by the human c-Met oncogene is expressed in hepatocytes, epithelial cells, and solid tumors. *Int. J. Cancer.* 1991;49:323–328.

Raymond G. M., Jumblatt M. M., Bartels S. P., Neufeld A. H. Rabbit corneal endothelial cells in vitro: effects of epidermal growth factor. *Invest. Ophthalmol. Vis. Sci.* 1986;27:474–9.

Reim M., Busse S., Leber M., Schulz C. Effect of epidermal growth factor in severe experimental alkali burns. *Ophthalmic. Res.* 1988;20:327–31.

Rich L. F., Hatfield J. M., Louiselie I. The influence of epidermal growth factor on cat corneal endothelial wound healing. *Curr. Eye. Res.* 1991;10:823–30.

Rubin J. S., Chan A. M. L., Bottaro D. P., Burgess W. H., Taylor W. G., Cech A. C., Hirschfield D. W., Wong J., Miki T., Finch P. W., and Aaronson S. A. A broad-spectrum human lung fibroblast-derived mitogen is a variant of hepatocyte growth factor. *Proc. Natl. Acad. Sci.* (USA). 1991;88:415–419.

Rubin J. S., Osada H., Finch P. W., Taylor W. G., Rudikoff S., and Aaronson S. A. Purification and characterization of a newly identified growth factor specific for epithelial cells. *Proc. Natl. Acad. Sci.* (USA) 1989;86:802–806.

Soong H. K., Hassan T., Varani J., Huang S. C., Brennan M. Fibronectin does not enhance epidermal growth factor-mediated acceleration of corneal epithelial wound closure. *Arch. Ophthalmol.* 1989;107:1052–4.

Weidner K. M., Arakaki N., Hartmann G., Vandekerkhove J. Evidence for the identity of human scatter factor and human hepatocyte growth factor. *Proc. Natl. Acad. Sci.* 1991;88:7001–7005.

Wilson S. E., He Y.-G., Lloyd S. A. Epidermal growth factor, epidermal growth factor receptor, basic FGF, TGF beta-1, and IL-1 alpha messenger RNA production in human corneal epithelial cells and stromal fibroblasts. *Invest. Ophthalmol. Vis. Sci.* 1992;33:1756–1765.

Wilson S. E., Lloyd S. A., He Y.-G., McCash C. S. Extended Life of Human Corneal Endothelial Cells Transfected with the SV40 Large T Antigen. *Invest. Ophthalmol. Vis. Sci.* In press.

Wilson S. E., Lloyd S. A. Epidermal Growth Factor and its Receptor, Basic Fibroblast Growth Factor, Transforming Growth Factor beta-1, and Interleukin-1 Alpha Messenger RNA Production in Human Corneal Endothelial Cells. *Invest. Ophthalmol. Vis. Sci.* 1991;32:2747–2756.

What is claimed is:

1. A method for promoting corneal cell proliferation or maintaining corneal cell viability in vivo comprising treating the corneal cells with an amount of hepatocyte growth factor to stimulate growth in a pharmaceutically acceptable composition.

2. The method of claim 1 wherein cells located on the corneal posterior surface are treated.

3. The method of claim 1 wherein cells located in corneal central regions are treated.

4. The method of claim 1 wherein the pharmaceutically acceptable composition further comprises keratinocyte growth factor.

5. The method of claim 4 wherein each growth factor is present between about 1 and about 50 nanograms per ml.

6. The method of claim 4 wherein each growth factor is present between about 1 and about 25 ng/ml.

7. The method of claim 4 wherein each growth factor is present between about 1 and about 10 ng/ml.

8. A pharmaceutical composition comprising hepatocyte growth factor and keratinocyte growth factor in a pharmaceutically acceptable carrier.

9. The composition of claim 8 wherein the amount of each growth factor is between about 1 and about 50 nanograms per ml.

10. The composition of claim 8 wherein the amount of either growth factor is between about 1 and about 25 ng/ml.

11. The composition of claim 8 wherein the amount of either growth factor is between about 1 to about 10 ng/ml.

12. A method of suppressing hepatocyte growth factor stimulated corneal cell proliferation in culture comprising treating said corneal cells with an amount of calcium ion effective to suppress corneal cell proliferation.

13. The method of claim 12 wherein the corneal cells are treated with about 0.1 mM calcium ion.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GAAGTCCAGG GCGACGTAGC AC        22

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGTACTGTGC AATTAAAACA TGCG        24

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTGTTTGGGA TAAGTTGCCC A        21

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAGTTGTTTC CATAGGAACA TCAGTATCAT        30

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGGTCCTTTG GCGTCGTCCT C                                                         21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTCATCATCA GCGTTATCTT C                                                         21

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CTTTAGGGTG CCAGCATTTT AGCATTACTT                                                30

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCCACACTAA CTATGGAAAA TG                                                        22

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTCCAGGATT TGCTGGCCCA AGT                                                       23

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCATAGGAAA AAAGCATGAT TATTTGTGGG                                                30

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGATCAAGCA CGTGGAAAAG A                                                         21

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GCCCTATATA ATTGGAGACC T                                             21

( 2 ) INFORMATION FOR SEQ ID NO:13:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GCCTCGGTCA CATTGAACAG AGCCAGCACT                                    30

( 2 ) INFORMATION FOR SEQ ID NO:14:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

ACCATGCAGA GTGAAAGGAT A                                             21

( 2 ) INFORMATION FOR SEQ ID NO:15:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

GTTACATTCC GAATATAGAG AACCTCAATC                                    30